United States Patent
Hong et al.

(10) Patent No.: US 11,697,131 B2
(45) Date of Patent: Jul. 11, 2023

(54) METHOD FOR MODIFYING SURFACE OF POLYMER SUBSTRATE AND POLYMER SUBSTRATE HAVING SURFACE MODIFIED THEREBY

(71) Applicants: INDUSTRY-UNIVERSITY COOPERATION FOUNDATION HANYANG UNIVERSITY ERICA CAMPUS, Gyeonggi-do (KR); CEKO CO., LTD., Gyeonggi-do (KR)

(72) Inventors: Jong Wook Hong, Seoul (KR); Soo Jeong Shin, Seoul (KR); Hyun Joong Kim, Seoul (KR); Hong Chul Kim, Seoul (KR); Jeong Rae Kim, Seoul (KR); Byeong Gyeong Choi, Gyeonggi-do (KR); Cheol Min Kim, Gyeonggi-do (KR)

( * ) Notice: Subject to any disclaimer, the term of this patent is extended or adjusted under 35 U.S.C. 154(b) by 130 days.

(21) Appl. No.: 16/490,778

(22) PCT Filed: Mar. 3, 2017

(86) PCT No.: PCT/KR2017/002356
§ 371 (c)(1),
(2) Date: Oct. 24, 2019

(87) PCT Pub. No.: WO2018/159886
PCT Pub. Date: Sep. 7, 2018

(65) Prior Publication Data
US 2020/0147567 A1    May 14, 2020

(30) Foreign Application Priority Data
Mar. 3, 2017  (KR) .................. 10-2017-0027618

(51) Int. Cl.
| | | |
|---|---|---|
| *B05D 3/14* | (2006.01) | |
| *B01J 2/30* | (2006.01) | |
| *B05D 7/24* | (2006.01) | |
| *C08J 7/043* | (2020.01) | |
| *C08J 7/056* | (2020.01) | |
| *C09D 183/08* | (2006.01) | |
| *G01N 33/68* | (2006.01) | |

(52) U.S. Cl.
CPC ................ *B05D 3/144* (2013.01); *B01J 2/30* (2013.01); *B05D 7/24* (2013.01); *C08J 7/043* (2020.01); *C08J 7/056* (2020.01); *C09D 183/08* (2013.01); *G01N 33/68* (2013.01)

(58) Field of Classification Search
CPC .. B05D 3/144; B05D 7/24; C08J 7/056; C08J 7/043; C09D 183/08
See application file for complete search history.

(56) References Cited

U.S. PATENT DOCUMENTS

| | | | | |
|---|---|---|---|---|
| 4,808,483 A | * | 2/1989 | Nakasuji | C08G 59/145 427/299 |
| 5,888,656 A | * | 3/1999 | Suzuki | C08J 7/12 428/425.5 |
| 6,793,759 B2 | * | 9/2004 | Chaudhury | C09J 5/02 156/272.6 |
| 2004/0071987 A1 | * | 4/2004 | Bate | C08J 7/04 428/447 |
| 2012/0251728 A1 | * | 10/2012 | Kuwata | C09D 183/08 106/2 |
| 2016/0137852 A1 | | 5/2016 | Lin et al. | |
| 2017/0210916 A1 | * | 7/2017 | Uotani | A43B 7/12 |

FOREIGN PATENT DOCUMENTS

| | | |
|---|---|---|
| CN | 1135649 | 11/1996 |
| KR | 10-2011-0055904 | 5/2011 |
| KR | 10-2016-0061348 | 5/2016 |
| KR | 10-2016-0119288 | 10/2016 |
| KR | 10-2016-0123540 | 10/2016 |

OTHER PUBLICATIONS

International Search Report, dated Nov. 30, 2017 in corresponding International Patent Application No. PCT/KR2017/002356, with English language translation.
Office Action dated Aug. 3, 2021 in Chinese Patent Application No. 201780090368.3.

* cited by examiner

*Primary Examiner* — Michael P Wieczorek
(74) *Attorney, Agent, or Firm* — Wenderoth, Lind & Ponack, L.L.P.

(57) ABSTRACT

The present invention relates to a method for modifying the surface of a polymer substrate. Specifically, the present invention provides a method for modifying the surface of a polymer substrate using a plasma treatment, a hydrophilic primer and a coating agent including a hydrophobic fluorine compound.

12 Claims, 8 Drawing Sheets

Figure 4 a) BSA ADSORBED b) BSA NOT ADSORBED

METHOD FOR MODIFYING SURFACE OF POLYMER SUBSTRATE AND POLYMER SUBSTRATE HAVING SURFACE MODIFIED THEREBY

TECHNICAL FIELD

The present invention relates to a method for modifying the surface of a polymer substrate, and particularly, to a method for modifying the surface of a polymer substrate using plasma, a hydrophilic primer and a coating agent including a hydrophobic fluorine compound.

BACKGROUND ART

A biochip means a hybrid device made, in the form of an existing semiconductor chip, by combining biological organic materials such as enzymes, proteins, antibodies, DNAs, microorganisms, or animal and plant cells and organs derived from organisms, and nerve cells and organs with inorganic materials such as semiconductors or glass. The biochip diagnoses an infectious disease or analyzes a gene by utilizing the unique functions of a biomolecule and imitating the functions of a living organism, and serves as a new functional device for information processing. The biochip may be defined extensively, including a biosensor that may serve to detect and analyze various biochemical materials like a lab-on-a-chip which is compactly integrated and thus has automatic analysis functions, so as to perform preprocessing, biochemical reaction, detection, and data analysis of a sample.

The biochip may be applied to various fields such as microchips, medical devices, medical materials, and SPF facilities, and a technology for modifying the surface of a polymer substrate that is one of the constituent materials of the biochip, particularly, a silicone polymer substrate is a basic fundamental technology whose importance is very high.

Polydimethylsiloxane (PDMS), which is one of the silicone polymers, has been widely used as a basic material for the manufacture of a lab-on-a-chip in which biotechnologies are fused, in addition to existing microarray and micro/nanofluidic systems, due to various advantages such as transparency of materials, flexibility of materials, non-toxicity to cells, ease of manufacture, and low manufacturing costs.

However, despite these advantages of PDMS, PDMS has not been widely used as a material for a chip that is finally commercialized, and the problem of sample adsorption onto PDMS chips is the biggest cause. PDMS is in the form in which $-OSi(CH_3)_2-$ is repeated, and has a hydrophobic surface due to the $-CH_3$ group among them, but due to the unique viscosity thereof, the adsorption of a hydrophobic material is very strong, and it is difficult to desorb a material that is adsorbed once. In order to analyze a single nanoparticle and a trace of material, it is extremely necessary to prevent the adsorption that may serve as the noise of the experimental result, and particularly, since a biological sample such as a protein and a cell includes a part of a hydrophobic group on the surface thereof, there occurs a problem in some cases in that the biological sample is easily adsorbed onto the surface of the PDMS and the unique 3-dimensional structure thereof is deformed. In contrast, it is difficult to attach cells to the surface of the PDMS and culture cells due to the hydrophobic surface thereof, and even when selectivity is imparted to the surface thereof using specific compounds, antibodies, and the like, a surface treatment procedure including various steps is required.

In order to improve this problem, attempts to modify the surface of a polymer substrate by performing a plasma treatment on the surface of a polymer substrate such as PDMS, adsorbing a non-specific protein onto the surface of the polymer substrate, or using a material including Teflon or a fluorocarbon group, which is similar to Teflon, have been continuously made.

However, oxygen plasma that has been used most widely provides a superhydrophilic surface, but has a short maintenance time of the hydrophilic surface, makes the surface of the PDMS rough, or forms even cracks, so that there is a problem in that the oxygen plasma is not suitable for an experiment using relatively small particles such as nanoparticles in microchips. In addition, in the case of a fluorine compound-based coating agent publicly known to be used for glass or plastic in the related art, a disadvantage has been found in that the coating agent forms a hard-coating layer after being dried to degrade the flexibility of a polymer substrate or a coating layer is broken by the movement of the polymer substrate.

The present invention has been completed in order to lay a foundation that opens up the possibility of observing a genuine single molecule by preventing the adsorption of such a non-specific biological molecule and a foreign material such as a particle, and accordingly, it is expected to increase the scope of a bio experiment in which a biochip based on a polymer such as silicone may be applied as a platform.

DETAILED DESCRIPTION OF INVENTION

Technical Problem

The present invention provides a method for modifying the surface of a polymer substrate, and particularly, a method for modifying the surface of a polymer substrate using a plasma treatment, a hydrophilic primer and a coating agent including hydrophobic fluorine compound.

Technical Solution

An aspect of the present invention provides a method for modifying a surface of a polymer substrate, the method including: treating the surface of the polymer substrate with plasma; applying a hydrophilic primer onto the surface of the plasma-treated polymer substrate; and coating the plasma-treated polymer substrate with a coating agent containing a hydrophobic fluorine compound.

Hereinafter, the polymer substrate will be described in detail.

According to an exemplary embodiment of the present invention, in the method of the present invention, the treating of the surface of the polymer substrate with plasma is first performed.

In the present step, the polymer substrate is put into a plasma reactor under the atmospheric pressure at room temperature, a gas is injected thereinto, and then plasma of the gas is formed by applying power to electrodes present at both ends of the plasma reactor.

According to an exemplary embodiment of the present invention, the plasma may be plasma of argon, nitrogen, oxygen, or a mixed gas in which two or more of these gases are mixed. Further, the plasma may be low-temperature or high-temperature plasma, and is preferably plasma produced at low temperature. A hydrophilically modified surface may be obtained by treating the surface of the polymer substrate with plasma, and the subsequent bonding of a coating agent may occur more strongly and safely.

According to an exemplary embodiment of the present invention, in the treating of the surface of the polymer substrate with plasma, the plasma is formed by applying power using RF power at 700 to 800 W, using a mixed gas of argon and oxygen at an atmospheric pressure (760 Torr), thereby treating the surface of the polymer substrate with plasma reciprocally at a speed of 15 mm/sec.

According to an exemplary embodiment of the present invention, the polymer substrate may include a natural or artificial polymer prepared by condensation or addition polymerization of one or more monomers, and may include preferably a siloxane-based polymer, more preferably silicone rubber, an acrylic resin, a polystyrene resin, a polyvinyl chloride resin, a polyethylene resin, a polypropylene resin, nylon, a phenol resin, a melamine resin, an urea resin, or an epoxy resin, and even more preferably a hydrophobic resin, a fluorine polymer, an acrylic resin, or a polyethylene resin, but is not limited thereto.

According to an exemplary embodiment of the present invention, the method may further include applying a hydrophilic primer onto the surface of the polymer substrate after the treating of the surface of the polymer substrate with plasma.

According to an exemplary embodiment of the present invention, the applying of the hydrophilic primer onto the surface of the polymer substrate is performed after the treating of the surface of the polymer substrate with plasma.

According to an exemplary embodiment of the present invention, the primer may include a condensed polymer of a silicone-based polymer and a functional organic or inorganic silane compound.

As used herein, the "primer" is a buffer coating layer that is applied in a nano-thickness between a substrate and a functional coating layer to improve adhesion, and may be a polycondensation reaction product of a silicone-based polymer and a functional organic or inorganic silane compound.

As used herein, the "silicone-based polymer" may be specifically selected from a modified silicone polymer having one or more reactive groups selected from an amino group, an epoxy group, a carboxyl group, a carbinol group, a methacryl group, a mercapto group, and a phenyl group, and a combination thereof, and may be preferably a polymer of aminoalkylsilane.

The "functional organic or inorganic silane compound" as a constituent of the primer used in the present specification may be an organic or inorganic silane compound having one or more of reactive groups which performs a polycondensation reaction with the silicone-based polymer, for example, an amino group, a vinyl group, an epoxy group, an alkoxy group, a halogen group, a mercapto group, a sulfide group, and the like. Specifically, the functional organic or inorganic silane compound may be selected from aminopropyltriethoxysilane, aminopropyltrimethoxysilane, aminomethoxysilane, phenylaminopropyltrimethoxysilane, N-(2-aminoethyl)-3-aminopropyltrimethoxysilane, N-(β-aminoethyl)-γ-aminopropylmethyldimethoxysilane, γ-aminopropyltridimethoxysilane, γ-aminopropyldimethoxysilane, γ-aminopropyltriethoxysilane, γ-aminopropyldiethoxysilane, vinyltriethoxysilane, vinyltrimethoxysilane, vinyltri(methoxyethoxy)silane, di-, tri- or tetraalkoxysilane, vinylmethoxysilane, vinyltrimethoxysilane, vinylepoxysilane, vinyltriepoxysilane, 3-glycidoxypropyltrimethoxysilane, 3-methacryloxypropyltrimethoxysilane, γ-glycidoxypropyltriethoxysilane, γ-methacryloxypropyltrimethoxysilane, chlorotrimethylsilane, trichloroethylsilane, trichloromethylsilane, trichlorophenylsilane, trichlorovinylsilane, mercaptopropyltriethoxysilane, trifluoropropyltrimethoxysilane, bis(trimethoxysilylpropyl)amine, bis(3-triethoxysilylpropyl) tetrasulfide, bis(triethoxysilylpropyl)disulfide, (methacryloxy)propyltrimethoxysilane, 2-(3,4-epoxycyclohexyl)ethyltrimethoxysilane, 3-glycidoxypropylmethyldiethoxysilane, 3-glycidoxypropyldiethoxysilane, 3-glycidoxypropyltriethoxysilane, p-styryltrimethoxysilane, and a combination thereof, may be preferably selected from aminopropyltriethoxysilane and a combination including the same, but is not limited thereto.

The primer is applied by a wet process, and is applied by completely dissolving a hydrophilic primer in a solvent, specifically, ethanol, and then applying the resulting solution onto the surface of the polymer substrate. The application includes painting, spraying, dipping, and the like, and may be preferably performed by spraying.

Thereafter, the coating of the surface of the polymer substrate with the coating agent containing the hydrophobic fluorine compound will be performed.

As used herein, the term "fluorine compound" broadly refers to a compound including a fluorine (F) atom in the compound, and includes a single compound and a polymerized compound. Preferably, the fluorine compound includes a fluorine-based organic component, and exhibits hydrophobicity.

According to an exemplary embodiment of the present invention, the fluorine compound may be a product of a polycondensation reaction of a fluorine-based polymer and a functional organic or inorganic silane compound.

As used herein, the "fluorine-based polymer" may be a perfluorinated polymer. Specifically, the fluorine-based polymer may be selected from the group consisting of a polymer including tetrafluoroethylene, hexafluoropropylene, chlorotrifluoroethylene, trifluoroethylene, vinylidene fluoride, octafluorobutylene, pentafluorophenyl trifluoroethylene, pentafluorophenyl ethylene, and a repeat unit induced from the monomer, a fluoro-containing acrylate polymer, and perfluoro polyether, and may be preferably perfluoro polyether, but is not limited thereto.

The "functional organic or inorganic silane compound" as a constituent of the fluorine compound used in the present specification may be an organic or inorganic silane compound having one or more of reactive groups which performs a polycondensation reaction with the fluorine-based polymer, for example, an amino group, a vinyl group, an epoxy group, an alkoxy group, a halogen group, a mercapto group, a sulfide group, and the like. Preferably, the functional organic or inorganic silane compound may be selected from the group consisting of an organic silane including an alkoxy group, a silane compound including a functional organic group, and a partial hydrolysis condensate of an organic silane composition. Specifically, the functional organic or inorganic silane compound may be selected from aminopropyltriethoxysilane, aminopropyltrimethoxysilane, amino-methoxysilane, phenylaminopropyltrimethoxysilane, N-(2-aminoethyl)-3-aminopropyltrimethoxysilane, N-(β-aminoethyl)-γ-aminopropylmethyldimethoxysilane, γ-aminopropyltridimethoxysilane, γ-aminopropyldimethoxysilane, γ-aminopropyltriethoxysilane, γ-aminopropyldiethoxysilane, vinyltriethoxysilane, vinyltrimethoxysilane, vinyltri(methoxyethoxy)silane, di-, tri- or tetraalkoxysilane, vinylmethoxysilane, vinyltrimethoxysilane, vinylepoxysilane, vinyltriepoxysilane, 3-glycidoxypropyltrimethoxysilane, 3-methacryloxypropyltrimethoxysilane, γ-glycidoxypropyltriethoxysilane, γ-methacryloxypropyltrimethoxysilane, chlorotrimethylsilane, trichloroethylsilane, trichloromethylsilane, trichlorophenylsilane, trichlorovinylsilane, mercaptopropyltriethoxysilane, trifluoropropyltrimethoxysilane, bis(trimethoxysilylpropyl)amine, bis(3-triethoxysilylpropyl)tetrasulfide, bis(triethoxysilylpropyl)disulfide, (methacryloxy)propyltrimethoxysilane, 2-(3,4-epoxycyclohexyl)ethyltrimethoxysilane, 3-glycidoxypropylmethyldiethoxysilane, 3-glycidoxypropyldiethoxysilane, 3-glycidoxypropyltriethoxysilane, p-styryltrimethoxysilane, and a combination thereof, may be preferably aminopropyltriethoxysilane and a combination including the same, but is not limited thereto.

The coating is preferably performed by a wet process, and is performed by completely dissolving a hydrophobic fluorine compound in a solvent, specifically, a fluorine-based solvent (HFE7200, 3 M), and then applying the resulting solution to the surface of the polymer substrate. The application includes painting, spraying, dipping, and the like, and may be preferably performed by spraying.

An aspect of the present invention provides a polymer substrate whose surface is modified by the method.

An aspect of the present invention provides a biochip including the polymer substrate. The biochip may be specifically a microarray or a microfluidic chip. The biochip may be prepared by additionally attaching enzymes, proteins, antibodies, DNAs, compounds, and the like, which are capable of detecting various biological molecules and derived from an organisms, onto the polymer substrate according to the present invention, and the biochip may detect the presence and absence of and/or the concentration of a target material to be detected by various physical and chemical methods such as electrochemistry, fluorescence, SPR, FET, and a thermal sensor.

Advantageous Effects

By modifying the surface of a hydrophobic polymer substrate according to the present invention, it is possible to remarkably enhance, without impairing the transparency, flexibility, and the like of a material, which are advantages of a device, an apparatus, and the like including an existing hydrophobic polymer substrate, an effect of preventing a non-specific biological molecule and a foreign material, such as a particle, from being adsorbed onto the surface of the device, and the like.

In addition, while maintaining the transparency and flexibility of a material, the cell viability, and the like, which are advantages of a device, an apparatus, and the like including an existing hydrophobic polymer substrate, it is possible to provide a polymer substrate in which an effect of preventing a non-specific biological molecule, such as a protein and a cell and a foreign material, such as a particle, from being adsorbed onto the device, the apparatus, and the like is remarkably enhanced, and furthermore, a biochip including the same.

BEST MODE

An aspect of the present invention provides a method for modifying a surface of a polymer substrate, the method including: treating the surface of the polymer substrate with plasma; applying a hydrophilic primer onto the surface of the plasma-treated polymer substrate; and coating the plasma-treated polymer substrate with a coating agent containing a hydrophobic fluorine compound.

MODE FOR INVENTION

Hereinafter, the present invention will be described in more detail through one or more Examples. However, these Examples are provided only for exemplarily explaining one or more Examples, and the scope of the present invention is not limited by these Examples.

Example 1

Surface Modification of PDMS Coin 1.1. Plasma Treatment of Surface of PDMS Coin

First, a PDMS coin with a diameter of 1.5 cm and a height of 0.5 cm was manufactured and subjected to a plasma treatment under an atmospheric pressure at room temperature, and the plasma-treated PDMS coin was used for the cleaning of organic contaminants and the surface modification.

For the plasma treatment, a mixed gas of 25 sccm of an argon (Ar) gas and 30 sccm of an oxygen ($O_2$) gas was used at an atmospheric pressure of 1 atm (760 Torr), and the formation of plasma was induced by applying power using RF power at 700 to 800 W, thereby treating the PDMS coin with plasma reciprocally at a speed of 15 mm/sec.

1.2. Coating of Surface of PDMS Coin Using Coating Agent WNP/WAF Containing Fluorine Compound After the PDMS coin which was plasma-treated in Example 1.1. was taken out of the plasma reactor and coated to have a thickness of about 10 to 20 nm by spraying Nano-Primer (NP, product name: CK-WNP, manufactured by CEKO, Inc.), purchased as an attachment reinforcing agent, at 40 ml/m$^2$ under a wet process, the resulting product was spray-coated with Wet Anti-fingerprint (WAF, product name: CK-WAF, manufactured by CEKO, Inc.), which is a hydrophobic compound purchased as a fluorine compound, at 35 ml/m$^2$ under a wet process, and then the coated-PDMS coin was dried by hot wind for about 1 hour (WNP/WAF method, in this case, W before NP and AF indicates that the coating is performed under a wet process). In the present Example 1.2., the Nano-Primer (NP) served as a buffer layer for enhancing attachment.

Comparative Example 1

Surface Modification 1 of PDMS Coin Using AF

The PDMS coin which was plasma-treated in Example 1.1. was taken out of the plasma reactor, coated to have a thickness of 12 nm using SiO$_2$, and then coated with 0.3 g of AF, as a hydrophobic compound, by an evaporative deposition using e-beam under a dry process (AF1 method). In this case, the formed hydrophobic coating foil had a thickness of about 20 to 30 nm. In the present Comparative Example 1, SiO$_2$ served as a buffer layer for enhancing attachment.

Comparative Example 2

Surface Modification 2 of PDMS Coin Using AF

The PDMS coin which was plasma-treated in Example 1.1. was taken out of the plasma reactor, coated to have a thickness of 5 nm using SiO$_2$, and then coated with 0.3 g of AF, as a hydrophobic fluorine compound, by a resistance heating element under a dry process (AF2 method). In the present Comparative Example 2, SiO$_2$ served as a buffer layer for enhancing attachment.

Comparative Example 3

Surface Modification of PDMS Coin Using WNP

The PDMS coin which was plasma-treated in Example 1.1. was taken out of the plasma reactor and sufficiently spray-coated with the resulting product obtained by completely dissolving 0.5 g of NP, as a hydrophilic compound containing a fluorine compound, in 100 g of ethanol as a solvent, such that the surface thereof was uniformly coated under a wet process, and then the coated-PDMS coin was dried by hot wind for 10 minutes (WNP method).

Experimental Example 1

Evaluation of Protein Adsorption after Surface Modification

A 0.01% (0.1 mg/ml) FITC-BSA stock was prepared by dissolving an FITC-BSA powder in DPBS, and 600 µl of a 0.01% FITC-BSA solution or 600 µl of a DPBS solution was placed on the coating surface of the PDMS coin that was surface-modified in Example 1, and then left to stand for 3 minutes. The PDMS coin was washed with DPBS for 1 minute, and then strongly washed with distilled water contained in a squeeze bottle for 1 minute, and the residual moisture thereof was removed by a blower. Thereafter, optical images and fluorescence images of the surface of the PDMS coin were captured, and the fluorescence quantification was performed using the ImageJ program.

Figure 1:
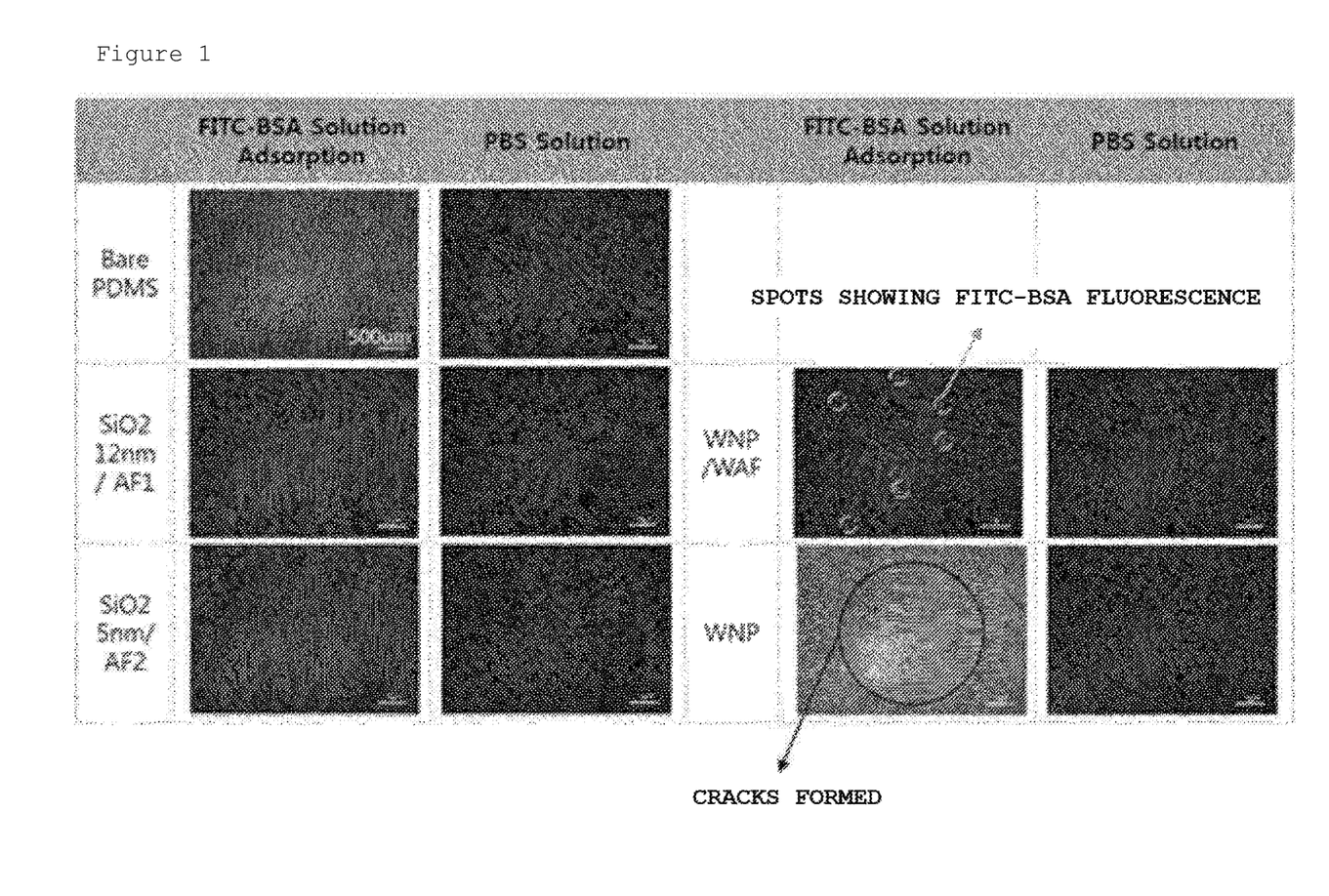
FIGS. 1 and 2 illustrate fluorescence photographs and relative fluorescence intensities exhibiting the adsorption degrees of FITC-BSA proteins of each of the PDMS biochips according to the present invention and Comparative Examples before and after the surface modification thereof.
Figure 2:
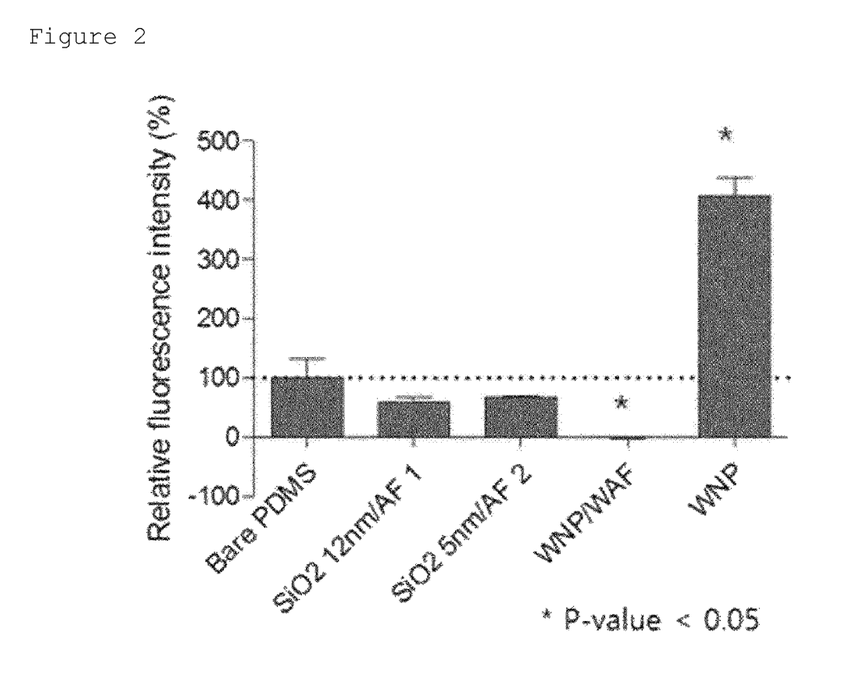

As a result, it could be confirmed that when the surface of the PDMS coin was coated with AF exhibiting hydrophobicity (Example 1 and Comparative Examples 1 and 2), the protein was scarcely adsorbed (<1%), whereas when the surface of the PDMS coin was coated with NP exhibiting hydrophilicity (Comparative Example 3), the protein was adsorbed at a high proportion (>400%). Further, when the surface of the PDMS coin was coated with NP (Comparative Example 3), cracks could be found in the absorption experiment (see FIGS. 1 and 2).

Experimental Example 2

Evaluation of Oil-Based Ink Adsorption after Surface Modification

On the surfaces of the PDMS coin onto which the protein was adsorbed (the PDMS coin that was left to stand in the 0.01% FITC-BSA solution) and of the PDM coin onto the protein was not adsorbed (the PDMS coin that was left to stand in the DPBS solution), which were prepared in Experimental Example 1, marks were drawn with a black oil-based ink pen at a predetermined speed, and the degree to which the oil-based ink was adsorbed onto the PDMS coin was observed.

Figure 3:
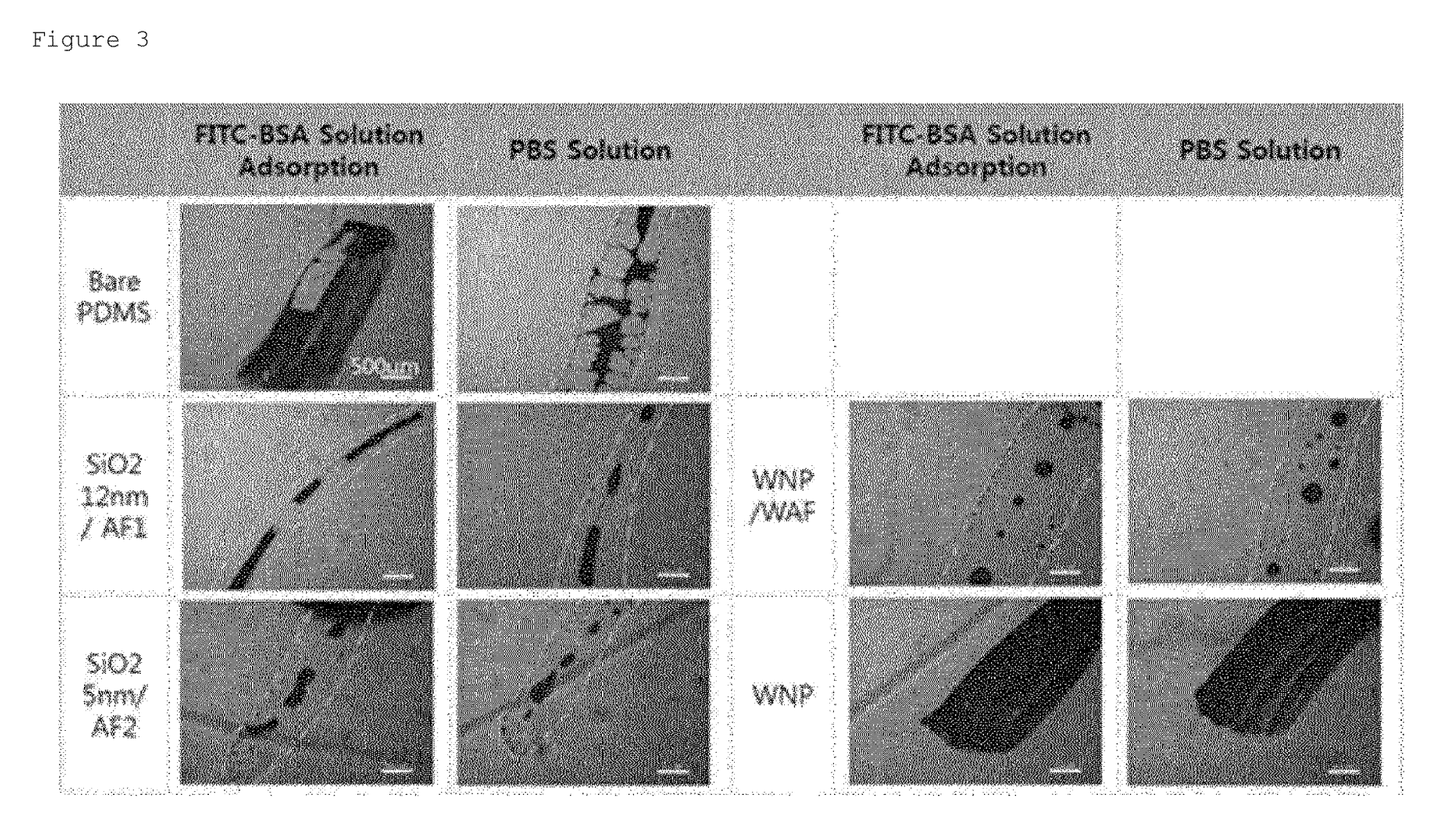
FIG. 3 illustrates the adsorption degree of an oil-based ink of each of the PDMS biochips according to the present invention and the Comparative Examples before and after the surface modification thereof, and the left side and the right side illustrate graphs of the case where a BSA protein is adsorbed and the case where a BSA protein is not adsorbed, respectively.

As a result, it could be confirmed that when the surface of the PDMS coin was coated with AF exhibiting hydrophobicity (Example 1 and Comparative Examples 1 and 2), the ink took the form of water droplets, whereas when the surface of the PDMS coin was coated with NP exhibiting hydrophilicity (Comparative Example 3), the ink was adsorbed in the form of the mark drawn with the oil-based ink pen. In particular, even among the hydrophobic coatings, it could be confirmed that the WNP/WAF method in which the PDMS coin was coated under a wet process had the strongest hydrophobicity, and simultaneously, the oil-based ink was aggregated in a form most similar to a perfect circle (see FIG. 3).

Experimental Example 3

Evaluation of Light Transmittance after Surface Modification

The change in light transmittance of each of the PDMS coin onto which the protein was adsorbed (the PDMS coin that was left to stand in the 0.01% FITC-BSA solution) and the PDM coin onto the protein was not adsorbed (the PDMS coin that was left to stand in the DPBS solution), which were prepared in Experimental Example 1, was observed using a UV-VIS spectrophotometer (HITACHI U-4100, 240 to 1,300 nm).

Figure 4:
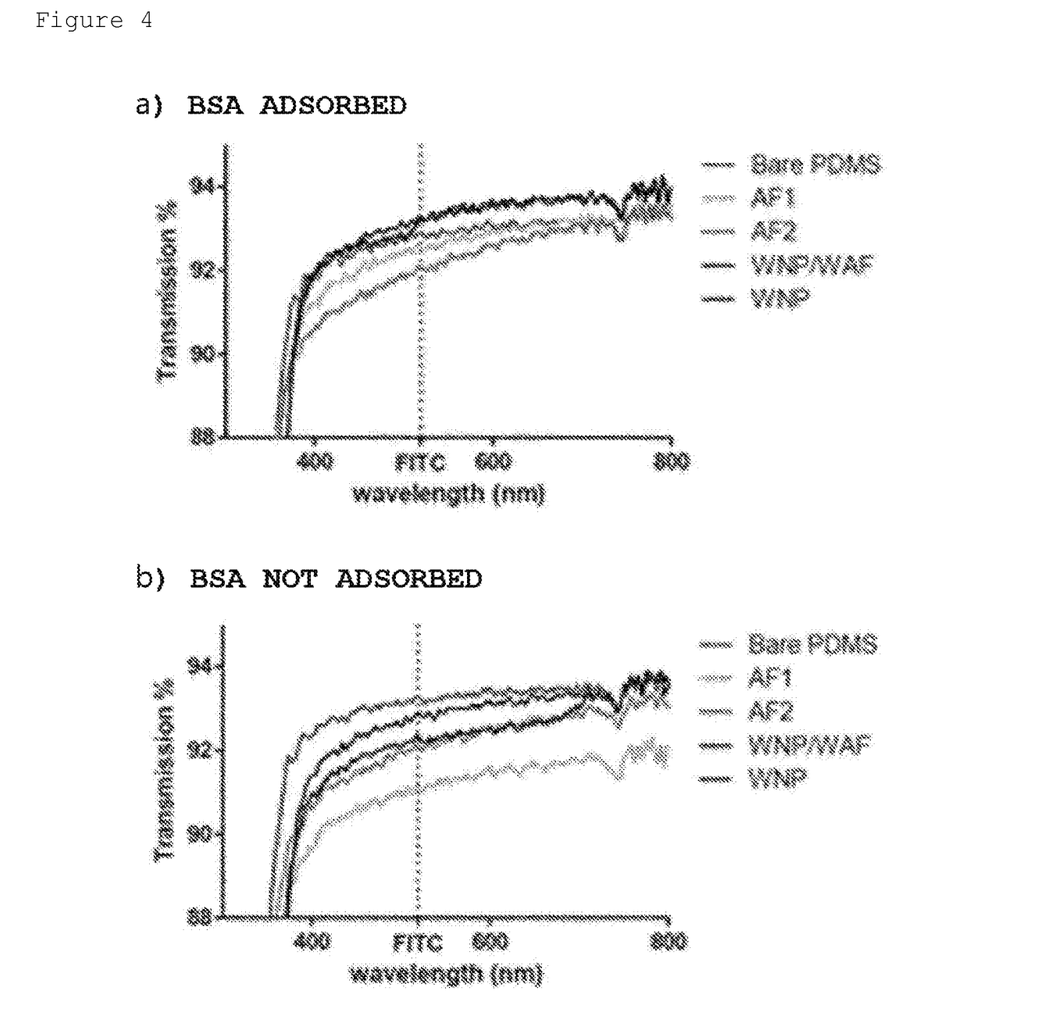
FIG. 4 illustrates the light transmittance of each of the PDMS biochips according to the present invention and the Comparative Examples before and after the surface modification thereof, and a) and b) illustrate graphs of the case where a BSA protein is adsorbed and the case where a BSA protein is not adsorbed, respectively.

As a result, when the protein was not adsorbed, the transmittance of the PDMS coin which was not treated was the best, the transmittance of Example 1 in which the PDMS coin was coated by the WNP/WAF method (the transmittance of the PDMS, subjected to surface modification coating, as compared to the bare PDMS: 98.27 to 99.89%) was the second best, and the transmittance of Comparative Example 3 in which the PDMS coin was coated by the WNP method (the transmittance of the PDMS, subjected to surface modification coating, as compared to the bare PDMS: 97.94 to 99.14%) was the third best (see FIG. 4A).

In contrast, it was determined that when the protein was adsorbed, the adsorption of the protein affected the light transmittance of the substrate (see FIG. 4B).

Experimental Example 4

Evaluation of Cell Viability after Surface Modification

Except that a PDMS sheet with a 100-pi dish size and a height of about 1 mm was used instead of the PDMS coin with a diameter of 1.5 cm and a height of 0.5 cm, the surface of the PDMS sheet was modified in the same manner as in the method described in Example 1.

The surface-modified PDMS sheet was disinfected with alcohol, and then washed with a medium to remove the residual alcohol. After the surface-modified PDMS sheet was placed on the bottom of the petri dish and 12 ml of the medium was put thereinto, about $4 \times 10^6$ MDA cells were inoculated thereto, and the resulting PDMS sheet was cultured for 3 days. After 3 days, cell attachment morphology and life and death determination tests were performed.

Figure 5:
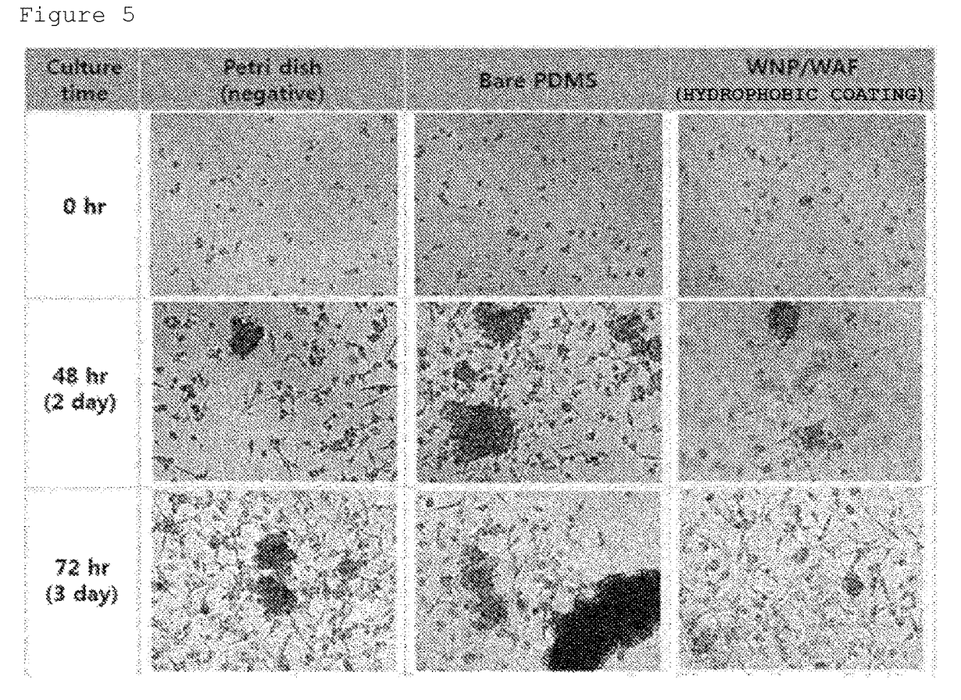
FIG. 5 illustrates morphological observation results of the MDA cell lines cultured on a petri dish (control), a PDMS whose surface is not modified, and the PDMS biochip according to the present invention (0 hour, 48 hours, and 72 hours).

As a result of observation of the cell attachment morphology, the MDA cells cultured on the PDMS coin sheet that was surface-modified by the method of the present invention were aggregated without being attached onto the surface of the PDMS to form a plurality of spheroids, and no significant difference were exhibited between the number and morphological shape of the observed cells and those of the cells cultured in the petri dish during the same period (see FIG. 5).

Figure 6:
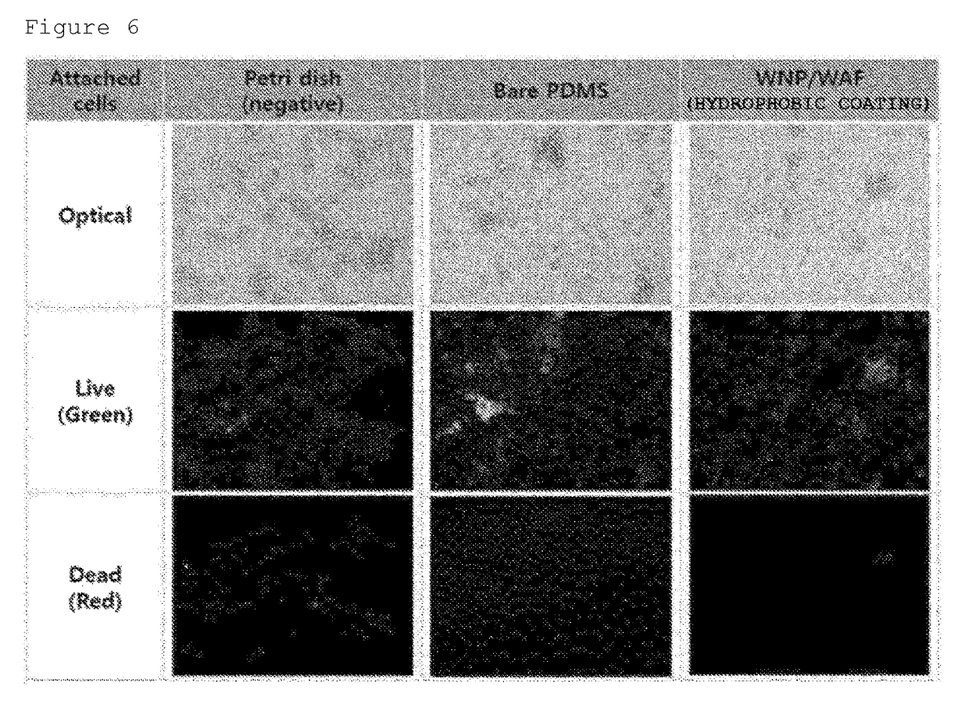
FIGS. 6 and 7 illustrate the life and death determination test results of cells attached to the bottom and cells floating in the medium, in the MDA cell lines cultured on a petri dish (control), a PDMS whose surface is not modified, and the PDMS biochip according to the present invention. The green color and the red color illustrate living cells and dead cells, respectively, and the number of the corresponding cells is proportional to the fluorescence intensity.
Figure 7:
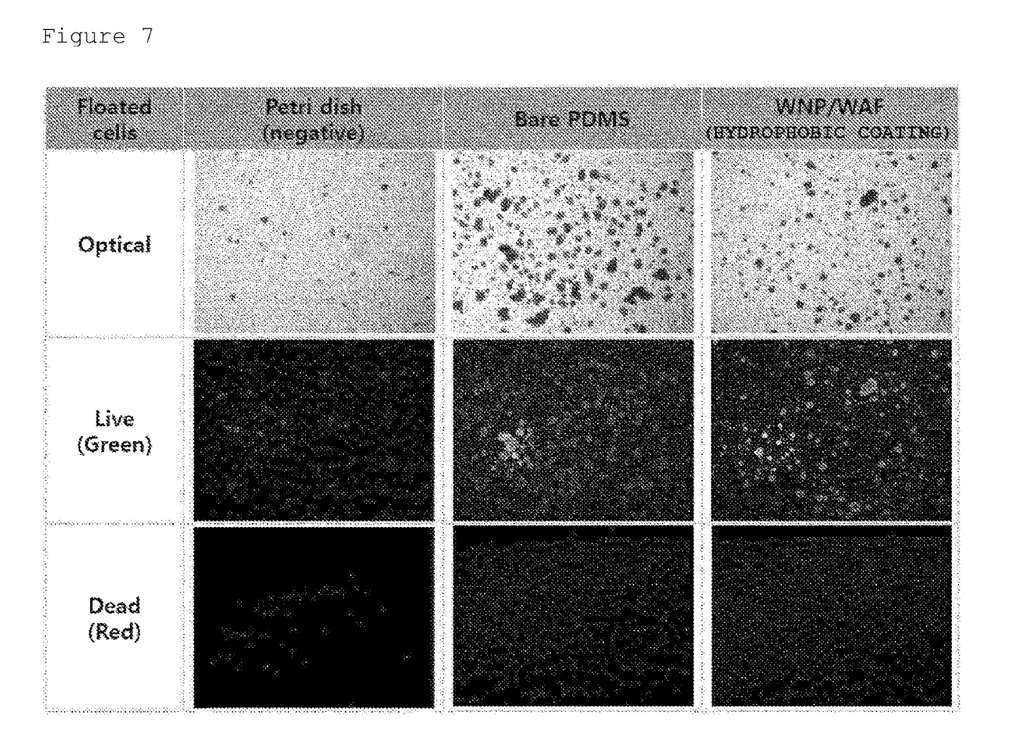
Figure 8:
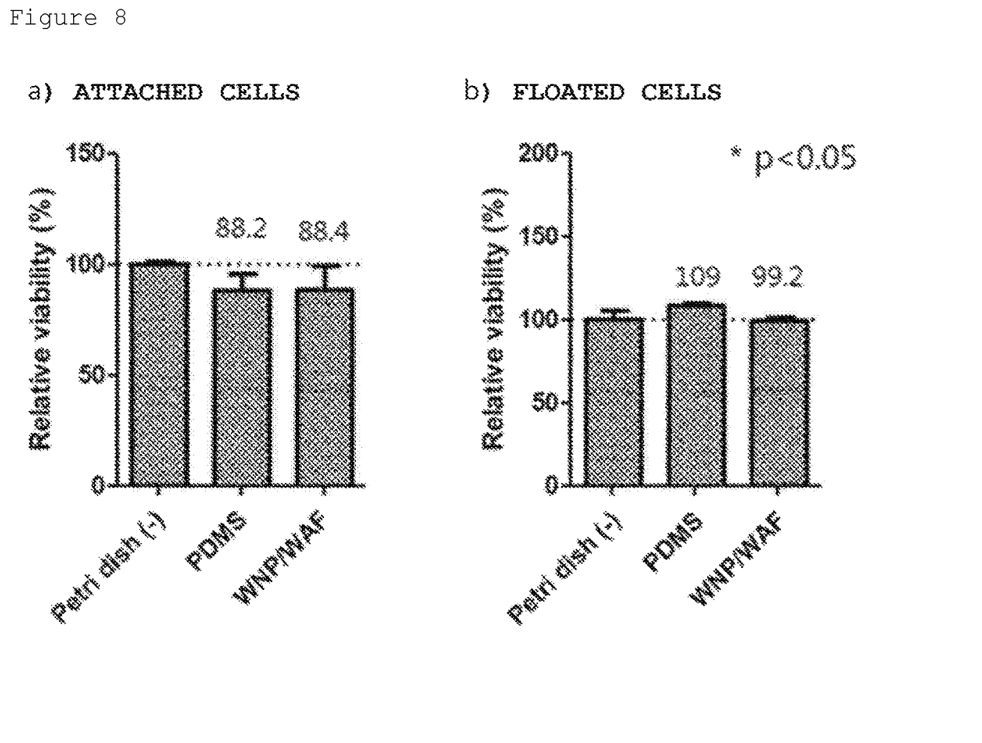
FIG. 8 illustrates a numerical comparison of the cell viability through the fluorescence intensities in FIGS. 6 and 7.

As a result of the cell life and death determination test, no significant difference was exhibited between the life and death of the attached cells cultured for 3 days in the PDMS coin sheet that was surface-modified by the method of the present invention and that of the cells cultured in the petri dish (88.4% as compared to the control). It could be confirmed that in the life and death of the cells floating in the medium, the cells cultured in the PDMS coins sheet that was surface-modified by the method of the present invention had a higher viability than that of the cells cultured in the petri dish (see FIGS. 6 to 8).

In addition, through the present experiment, it could be confirmed that the coating agent of the present invention did not show severe toxicity to the MDA cell line.

Experimental Example 5

Evaluation of Elasticity after Surface Modification

A PEEL test of measuring the elasticity by fixing the tension degree for 10 minutes was performed using a substrate prepared using a 20:1 PDMS.

Figure 9:
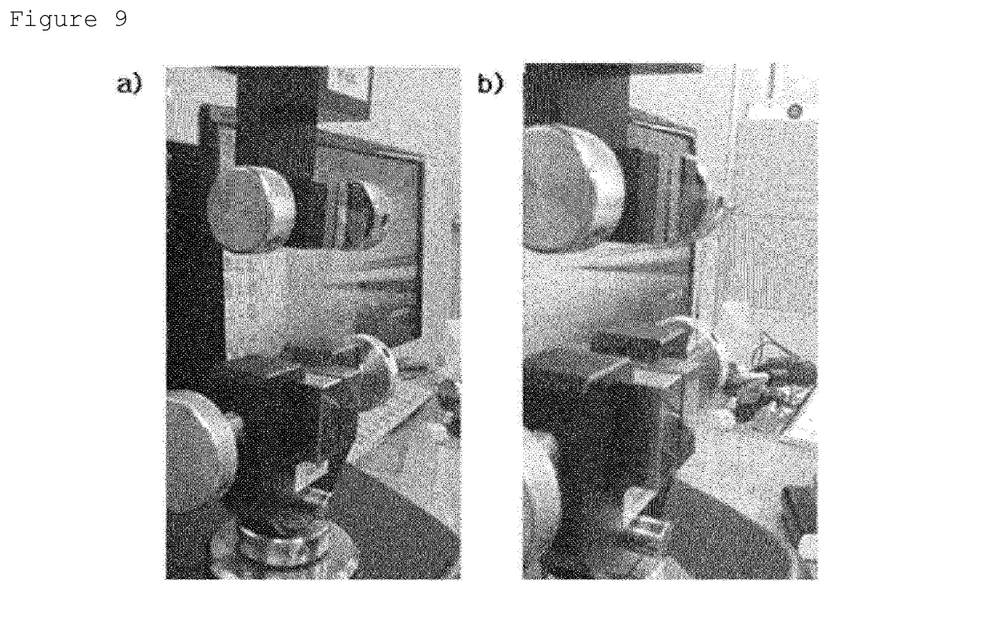
FIG. 9 illustrates PEEL test results of the PDMS substrate according to the present invention (a) during the experiment and b) after completion of the experiment.

It was confirmed that when both sides of the substrate were pulled out, the surface thereof was blurred, but a portion which was not tensioned maintained the transparency as it was (see FIG. 9A). After completion of the tension experiment for 10 minutes, it was confirmed that when the PDMS substrate returned to the original state thereof, the transparency returned to be almost equal to that before the experiment (see FIG. 9B).

Experimental Example 6

Preparation of Biocompatibility Biochip Having Modified Surface

First, a subspot material layer was formed by applying a dielectric material onto a substrate formed of PDMS, a photoresist was applied onto the subspot material layer, and then a specific pattern was formed by a lithography process. A biochip substrate having a desired structure was manufactured by etching the subspot material layer exposed by the pattern.

The biochip substrate was put into a plasma reactor under an atmospheric pressure at room temperature, and then treated with plasma as described in Example 1.1. Next, the plasma-treated biochip was sprayed with the resulting product obtained by completely dissolving 1 g of AF, as a fluorine compound, in 100 g of a fluorine-based solvent (HFE7200, 3 M), and the resulting biochip was dried, thereby completing a biochip substrate.

From the foregoing, the present invention has been reviewed mainly based on the preferred examples thereof. A person with ordinary skill in the art to which the present invention pertains will be able to understand that the present invention may be implemented in a modified form without departing from the essential characteristics of the present invention. Therefore, the disclosed examples should be considered not from a restrictive viewpoint, but from an explanatory viewpoint. The scope of the present invention is represented by the claims to be described below rather than the foregoing detailed description, and it should be interpreted that the meaning and scope of the claims and all the changes or modified forms derived from the equivalent concepts thereto fall within the scope of the present invention.

The invention claimed is:

1. A method for modifying a surface of a polymer substrate, the method comprising:
   treating the surface of the polymer substrate with plasma;
   applying a hydrophilic primer, under a wet process, comprising a polymer of aminoalkylsilane and a first functional organic or inorganic silane compound onto the surface of the plasma-treated polymer substrate; and
   hydrophobic coating the plasma-treated polymer substrate with a coating agent, under a wet process, containing a hydrophobic fluorine compound in a fluorine-based solvent comprising a condensed polymer of a fluorine-based polymer and a second functional organic or inorganic silane compound,
   wherein at least one of the first functional organic or inorganic silane compound and the second functional organic or inorganic silane compound is at least one compound selected from the group consisting of phenylaminopropyltrimethoxysilane, γ-aminopropyldimethoxysilane, γ-aminopropyldiethoxysilane, chlorotrimethylsilane, trichloroethylsilane, trichloromethylsilane, trichlorophenylsilane, trifluoropropyltrimethoxysilane, bis(trimethoxysilylpropyl)amine, bis(3-triethoxysilylpropyl)tetrasulfide, bis(triethoxysilylpropyl)disulfide, and p-styryltrimethoxysilane.

2. The method of claim 1, wherein the polymer substrate is a siloxane-based polymer.

3. The method of claim 2, wherein the siloxane-based polymer is silicone rubber.

4. The method of claim 1, wherein the plasma is plasma of argon, nitrogen, oxygen, or a mixed gas in which two or more of these gases are mixed.

5. The method of claim 1, wherein in the treating of the surface of the polymer substrate with plasma, the plasma is formed from a mixed gas by applying power using RF power at 700 to 800 W in a device in which pressure is maintained at an atmospheric pressure (760 Torr).

6. The method of claim 1, wherein the fluorine-based polymer is selected from the group consisting of a polymer comprising tetrafluoroethylene, hexafluoropropylene, chlorotrifluoroethylene, trifluoroethylene, vinylidene fluoride, octafluorobutylene, pentafluorophenyl trifluoroethylene, pentafluorophenyl ethylene, a fluoro-containing acrylate polymer, and perfluoro polyether.

7. The method of claim 1, wherein the second functional organic or inorganic silane compound comprises one or more functional groups selected from the group consisting of an amino group, a halogen group, and a sulfide group.

8. The method of claim 1, wherein the second functional organic or inorganic silane compound is at least one compound selected from the group consisting of phenylaminopropyltrimethoxysilane, aminopropyldimethoxysilane, γ-aminopropyldiethoxysilane, chlorotrimethylsilane, trichloroethylsilane, trichloromethylsilane, trichlorophenylsilane, trifluoropropyltrimethoxysilane, bis(trimethoxysilylpropyl)amine, bis(3-triethoxysilylpropyl)tetrasulfide, bis(triethoxysilylpropyl)disulfide, and p-styryltrimethoxysilane.

9. The method of claim 1, wherein the hydrophobic fluorine compound is selected from the group consisting of polytetrafluoroethylene, an ethylene-tetrafluoroethylene copolymer, a perfluoropolyether group-containing silane, a tetrafluoroethylene-hexafluoropropylene copolymer, a partial hydrolysis condensate of a fluorooxyalkylene group-containing polymer composition, a fluoropolymer composition, polyvinylidene fluoride, and a fluorine-containing organopolysiloxane.

10. The method of claim 1, wherein the first functional organic or inorganic silane compound is at least one compound selected from the group consisting of phenylaminopropyltrimethoxysilane, aminopropyldimethoxysilane, γ-aminopropyldiethoxysilane, chlorotrimethylsilane, trichloroethylsilane, trichloromethylsilane, trichlorophenylsilane, trifluoropropyltrimethoxysilane, bis(trimethoxysilylpropyl)amine, bis(3-triethoxysilylpropyl)tetrasulfide, bis(triethoxysilylpropyl)disulfide, and p-styryltrimethoxysilane.

11. A polymer substrate whose surface is modified by the method for modifying a surface of a polymer substrate according to claim 1.

12. A biochip comprising the polymer substrate of claim 11.

* * * * *